United States Patent [19]

Oester et al.

[11] Patent Number: 5,470,741
[45] Date of Patent: Nov. 28, 1995

[54] **MUTANT OF *GEOTRICHUM CANDIDUM* WHICH PRODUCES NOVEL ENZYME SYSTEM TO SELECTIVELY HYDROLYZE TRIGLYCERIDES**

[75] Inventors: Dean A. Oester, Cincinnati; Allen L. Hall, Amelia; Stephen J. Vesper, Kettering, all of Ohio

[73] Assignee: Henkel Corporation, Plymouth Meeting, Pa.

[21] Appl. No.: 918,328

[22] Filed: Jul. 22, 1992

[51] Int. Cl.$^6$ ............................... C12N 1/14; C12N 9/20
[52] U.S. Cl. ............................... 435/254.1; 435/254.11; 435/134; 435/198
[58] Field of Search ............................... 435/254.1, 911, 435/134, 198, 254.11

[56] References Cited

U.S. PATENT DOCUMENTS

| | | | |
|---|---|---|---|
| 4,275,011 | 6/1981 | Tanaka et al. | 260/410.7 |
| 4,275,081 | 6/1981 | Colemen et al. | 426/33 |
| 4,683,987 | 8/1987 | Sakata et al. | 187/9 E |
| 4,719,178 | 1/1988 | Macrae et al. | 435/135 |
| 4,861,716 | 8/1989 | Macrae et al. | 435/134 |

FOREIGN PATENT DOCUMENTS

| | | |
|---|---|---|
| 0243338 | 10/1987 | European Pat. Off. . |
| 59-93889 | 11/1985 | Japan . |
| WO8903419 | 4/1989 | WIPO . |

OTHER PUBLICATIONS

The Merck Index, 11th Edition, p. 868.
Osterberg, et al., "Lipase Catalyzed Transesterification Of Unsaturated Lipids In A Microemulsion", *JAOCS*, vol. 66, No. 9, 1989, pp. 1330–1333.
Wilcox, J. C., et al., "The Selective Release Of Violatile Acids From Butterfat By Microbial Lipases", *Journal Of Dairy Sciences*, vol. 38, 1955, pp. 775–781.
Alford, J. A., et al., "Lipolytic Activity Of Microorganisms At Low And Intermediate Temperature. III. Activity Of Microbial Lipases At Temperatures Below 0° C.", *J. Food Sci.*, vol. 26, 1961, pp. 518–524.
Alford, J. A., et al., "Production Of Microbial Lipases For The Study Of Triglyceride Structure", *JAOCS*, vol. 42, 1965, pp. 1038–1040.
Alford, J. A., et al., "Activity Of Microbial Lipases On Natural Fats And Synthetic Triglycerides", *Journal Of Lipid Research*, vol. 5, 1964, pp. 390–394.
Franzke, et al., "Zentralblatt Fuer Pharmakotherapie Und Laboratoriumsdiagnostik", 111(10):1025–1033 (1972).
Kroll, J., et al., "Studien ueber die Glyceridstruktur von Fetten", *Pharmazie*, vol. 28, 1973, pp. 263–269.
Iwai, M., et al., "Lipid Requirement For The Lipase Production By *Geotrichum candidum* Link", *Agr. Biol. Chem.*, vol. 37 (4), 1973, pp. 929–931.
Jensen, R. G., "Symposium: Microbial Lipolytic Enzymes", *Lipids*, vol. 9, No. 3, 1974, pp. 149–157.
Kroll, J., et al., "Preparation And Properties Of The Immobilized Lipase From *Geotrichum candidum*", *Die Nahrung*, vol. 24, No. 3, 1980, pp. 215–225.
Kimura, Y., et al., "Application Of Immobilized Lipase To Hydrolysis Of Triacylglyceride", *European Journal Of Applied Microbiology And Biotechnology*, vol. 17, 1983, pp. 107–112.
Chemical Abstract 104:108231f (Equiv. to JP 60,237,997), Ishida, et al., "Oleic Acid Production From Oils And Fats", Jpn. Kokai Tokyo Koho.
Hata, Y., et al., "Low Resolution Crystal Structure Of Lipase From *Geotrichum candidum* (ATCC34614)", *Journal Of Biochemistry*, vol. 86, No. 6, 1986, pp. 1821–1827.
Tahoun, M. K., et al., "Fatty Acid And Position Specificities Of An Intracellular Lipase From Geotrichum Candidum", *Fat Sci. Technol.*, 1987, pp. 318–320.
Piazza, G., et al., "Lipolysis Of Olive Oil And Tallow In An Emulsifier–Free Two–Phase System By The Lipase From Oat Seeds", *Biotechnology Letters*, vol. 11, No. 7, 1989, pp. 487–492.
Lazar, G. and Eirich, L. D., "Hydrolysis Of Tallow, Olive Oil And Coconut Oil By Extracellular, Intracellular And Membrane–Bound Microbial Lipases" (Conference Abstract), *Biological Chemistry Hoppe Seyler*, (1989), vol. 370, 9, p. 985 (Henkel).
Jacobsen, T., et al., "Production, Partial Purification, And Immunochemical Characterization Of Multiple Forms Of Lipase From *Geotrichum candidum*", *Enzyme Microb. Technol.*, vol. 11, 1989, pp. 90–95.
Baillargeon, M. W., et al., "Evaluation Of Strains Of *Geotrichum candidum* For Lipase Production And Fatty Acid Specificity", *Applied Microbiology And Biotechnology*, vol. 30, 1989, pp. 92–96.
Hills, M. J., et al., "Enzymatic Fractionation Of Evening Primrose Oil By Rape Lipsae: Enrichment Of Gamma–Linolenic Acid", *Biotechnology Letters*, vol. 11, No. 9,
Jacobsen, T., et al., "Substrate Specificity Of *Geotrichum candidum* Lipase Preparations", *Biotechnology Letters*, vol. 12, No. 2, 1990, pp. 121–126.
Kwon, D. Y. and Rhee, J. S., *JAOCS*, vol. 63, 1986, pp. 89–92.
Biochim, et Biophys, Acta, 1123(1), 24 Jan. 1992, Charton (List continued on next page.)

*Primary Examiner*—Marian C. Knode
*Assistant Examiner*—Francisco C. Prats
*Attorney, Agent, or Firm*—Ernest G. Szoke; Wayne C. Jaeschke; Frank S. Chow

[57] ABSTRACT

A mutant fungal strain, namely *G. candidum* NRRL Y-552, mutant known as Henkel 9-2-3-9 (ATCC 74170) produces a lipase called "UNLipase" providing a selectivity of 25:1 for oleic acid over palmitic acid by the assay procedure employed. UNLipase has a temperature range of operation of between 0 and 40 degrees Celsius (and no activity over 55 degrees Celsius). The optimum pH ranges are between 7.5 and 8.5. Magnesium cations increase activity, whereas calcium cations are inhibitory. The molecular weight of the protein appears to be 65 kDa by size exclusion chromatography. UNLipase shows a high degree of selectivity for hydrolysis, esterification and transesterification.

2 Claims, No Drawings

OTHER PUBLICATIONS et al., "Substrate . . . from *Geotrichum candidum* CMICC335426", pp. 59–64.

Eur. J. Biochem., 202(2), 1991, Sidebottom et al, "*Geotrichum candidum* . . . specificities", pp. 485–491.

Appl. Microbio. and Biotech., 30(2), Jan. 1989, Baillargeon et al, "Evaluation of strains of *Geotrichum candidum* . . . specificity," pp. 92–96.

Biotech. Letters, 13(12), Dec. 1991, Baillargeon et al, "Selective lipid hydrolysis . . . NRRL Y–553 lipase", pp. 871–874.

Lipids 26(10), Oct. 1991, Baillaregeon et al, "*Geotrichum candidum* NRRL Y5553 Lipase: . . . Specificity", pp. 831–836.

Lipids 25(12), Dec. 1990, Baillargeon, "Purification and Specificity . . . *Geotrichum candidum,*" pp. 841–848.

Canadian J. Microbiol. 38(1), Jan. 1992, Jacobson et al, "Separation and characterization . . . ATCC 66592", pp. 75–80.

Rehm et al., "Biotechnology, A Comprehensive Treatise", pub. 1981. Verlag Chemie (Weinheim), p. 297–299.

MUTANT OF *GEOTRICHUM CANDIDUM* WHICH PRODUCES NOVEL ENZYME SYSTEM TO SELECTIVELY HYDROLYZE TRIGLYCERIDES

FIELD OF THE INVENTION

The present invention relates to a novel mutant strain of *Geotrichum candidum* and a novel lipase produced by that strain, UNLipase which selectively hydrolyzes oleic acid esters at superior rates over other saturated and unsaturated fatty acid esters, such as palmitoleic, and stearic esters.

BACKGROUND OF THE INVENTION

Glyceride cleavage is typically performed in industry using high-temperature steam treatment which does not discriminate between saturated and unsaturated fatty acid or fatty acid chain length. The use of enzymes, particularly lipases, as catalysts for efficient glyceride splitting at mild, low energy-demanding conditions would offer many economic advantages over these prior methods. The use of a selective lipase for the preparation of high purity oleic acid from fats or oils containing low levels of oleic acid would offer additional economic advantages over these prior methods.

A. Lipases, Generally

Lipases are a group of enzymes belonging to the esterases, and are also called glyceroester hydrolases or acylglycerolacylhydrolases. These enzymes hydrolyze fat and oils (present in ester form, such as glycerides), yielding the base components of glycerol and fatty acids. These enzymes also catalyze digestion. Lipases are widely found throughout the plant and animal worlds, including molds, bacteria, milk and milk products, and animal tissues such as the pancreas. Lipases have been widely used to split fats without damaging sensitive constituents, such as vitamins or unsaturated fatty acids. (The Merck Index, p. 868).

Lipases generally have two types of specificity, positional specificity and fatty acid specificity. Positional specificity or regiospecificity permits some lipases to split the ester bonds at particular positions on the triglyceride backbone. *Aspergillus niger* lipases display this type of specificity. Hata et al., J. Biochem. 86:6, 1821–1827 (1986). Pancreatic lipase and *Pseudomonas fragi* lipase reportedly attack triglycerides at the 1-, 3-positions. Alford et al., JAOCS 42, 1038-40 (1961). An ideal lipase for total fat splitting would have the following properties: 1) broad substrate specificities, 2) no significant interferences, 3) high specific activity, 4) a degree of hydrolysis of 100%.

Fatty acid specificity is displayed by lipases which indiscriminately split all of the ester bonds. Certain amounts of fatty acid specificity have been found in some *Geotrichum candidum* lipases. Hata et al., J. Biochem. 86:6 1821–1827 (1986). These lipases are generally specific for certain chain length fatty acids or double bond positions. Osterberg et al., JAOCS, 66:9 (1989).

B. Prior Research on *Geotrichum Candidum* Lipases

*G. candidum* is a mold with septate mycelia, found growing on sour cream and cheese in a firm white mass. Jensen, Lipids, 9, 149–157 (1974). It has long been known for its relatively selective lipases. While extensive research has been performed on *G. candidum* lipases, little success has been achieved with regard to obtaining a truly selective lipase.

A close examination of the prior art indicates that, while it has been known that *G. candidum* lipase has selectivity for oleic acid containing triglycerides over short chain fatty acids and saturated fatty acids, no lipase has attained the level of oleic acid selectivity shown by the UNLipase, which means Unsaturation-specific Lipase, enzyme of the present invention. Please see the following discussion of the prior art.

DESCRIPTION OF THE PRIOR ART

The following is a brief description of *G. candidum* lipases culled from the scientific references as indicated.

Wilcox, J. C., Nelson, W. O. and Wood, W. A. J. Dairy Sci. 38:775 (1955). Jensen (1973) reports that this article contains the first hint that *Geotrichum Candidum* lipase is specific for cis-9-unsaturation since the lipase hydrolyzed olive oil but not butterfat. Jensen notes that the ability to characterize different free fatty acids was limited in 1955, so that the researchers could not analyze their results to see that mostly oleic acid had been freed from the oils.

Alford and Pierce, "Lipolytic Activity of Microorganisms at Low and Intermediate Temperature. III. Activity of Microbial Lipases at Temperatures below 0° C." J. Food Sci. 26:518–524 (1961). Alford reports the first studies on the specificity of *G. Candidum* lipase for unsaturated fatty acids in natural oils. Alford et al. demonstrates also that the specificity is increased at lower temperatures. Alford hypothesizes that this is due to the changing physical structure of the fat. The lipase hydrolyzed 73% of the substrate triglycerides into free oleic acid.

Alford and Smith, "Production of Microbial Lipases for the Study of Triglyceride Structure", JAOCS 42:1038–40 (1961) Reports a selective lipase from *G. candidum*. Alford and Smith suggest that *G. Candidum* lipases attack primarily unsaturated fatty acid linkages. However, subsequent reports have contradicted this observation, see Franzke et al. below.

Alford, J., Pierce, D. and F. Suggs, J. Lipid Res 5:390 (1964). This paper confirmed the specificity of *G. candidum* lipase for oleic acid with synthetic triglycerides as substrates. The level of specificity is far lower than that disclosed by the Henkel mutant strain.

Alford, J. and J. Smith, JAOCS, 52:1038 (1965). This article discussed improved production of *G. Candidum* through particular media, and did not explore the selectivity of the lipase for saturated and unsaturated fatty acids.

Franzke et al., Zentralblatt Fuer Pharmakotherapie Und Laboratoriumsdiagnostik, 111:1025–1033 (1972) described a selective lipase for *G. candidum* however, hydrolysis of butterfat resulted in the release of 24% palmitic acid as well. Also, the hydrolysis of palm oil released more than 70% saturated fat. See also, Kroll, J., Franzke, C., and Genz, S. Pharmazie 28:263 (1973) (isolation of a lipase with a M.W. of 32 kDA).

Iwai et al., "Lipid Requirement for the Lipase Production by *Geotrichum candidum* Link", Agri Biol Chem. 37:4, 929–931 (1973) The authors report the separation of lipase by 44-fold with an estimated molecular weight of 53–55,000 daltons. The lipase is characterized by requiring the presence of lipid (lipid induction) in the medium for production of the enzyme. The study focuses on the production of lipase, not the reactions it undergoes nor its selectivity.

Jensen, R. G., "Symposium Microbial Lipolytic Enzymes", Lipid (1974). This paper characterizes the positional and fatty acid specificity of a lipase isolated from Geotrichum. The particular strain of Geotrichum has been lost preventing the work from being repeated.

Kroll et al., "Preparation and Properties of the Immobilized Lipase for *Geotrichum candidum*" Die Nahrung, 24:215–225 (1980). Lipase for *G. candidum* (strain unknown) was isolated and immobilized on cellulose columns. Enzyme activity of 58–66% was reported, and fatty acid specificity remained unchanged.

Kimura et al., J. Appl. Microbiol. Biotechnol. 17:107 (1983).

Japanese Patent 59-93,889, "Method for Producing Oleic Acid", (1984). This patent deals with the general area of enzymatic hydrolysis of triglycerides with any of a number of enzymes coming from the "Diotrichum" microbe, which is assumed to be "Geotrichum". This patent deals more with the separation of the liberated acids than the selectivity and activity of the enzyme itself.

Ishida et al., "Oleic acid production for oils and fats", Jpn. Kokai Tokyo Koho, JP 60,237,997 (filed May, 1984). Edible oils and fats are reportedly hydrolyzed with *Diotrichum candida* lipid hydrolyzing enzyme at a rate of over 70%. The unhydrolyzed portion is then fractionated using steam and oil-water phase separation to produce oleic acid. This abstract highlights the difficulty of obtaining highly purified quantities of oleic acid, even in normal enzymatic systems. Ishida et al. was forced to resort to non-enzymatic separation techniques to achieve sufficient purity.

Hata et al., "Low Resolution Crystal Structure of Lipase from *Geotrichum candidum* (ATCC34614), " J. Biochem. 86:6, 1821–27 (1986) This study only discusses the structure of lipase from a different strain of *G. candidum*.

Tahoun, Fat Sci. Tech. (1987). Results demonstrated in this article report on a 2 fold increase in hydrolysis of triolein over the tripalmitin in a *G. candidum* lipase preparation. Also, the "mycelial" lipase isolated by Tahoun is different from the lipase of this invention. This conclusion is further supported by the high molecular weight of the Tahoun enzyme, namely 79 kDA (specific activity of 327).

Vandamme et al. "Cloning of the lipase gene of *Geotrichum candidum* in *Escherichia coli* and yeast", EP 243 338 (filed, Apr. 25, 1986). This abstract discusses mainly the cloning of a gene coding for *G. candidum* extracellular lipase. The abstract notes that such lipase "displays a unique specificity for fatty acids which have a cis-9 double bond" but does not give the source of this information. The abstract does not indicate which lipase has been sequenced as well.

EP 87-870055.8, "DNA sequence coding for specific lipase vectors for the expression thereof, microorganisms transformed by these vectors and use of these microorganisms for the production of the lipase", Labofina the patentee, describes a sequence which would give rise to a protein with a molecular weight of about 29 kDA and perhaps demonstrates the low "selectivity" which has been known for years. Although the patent has broad claims, there is very little support for the selectivity described therein.

PCT/US88/03480. Lubrizol Corp. describes the use of enzymes to hydrolyze sunflower oil and the separation of the high oleic acid product. According to this reported abstract, 88% to 94% hydrolysis using U.S. rugosa lipase (not *G. candidum*) was utilized against sunflower seed oil. Sunflower seed oil is an oil with high concentrations of oleic acid present in the triglycerides.

Piazza et al., "Lipolysis of Olive Oil and Tallow in an Emulsifier-Free Two-Phase System By the Lipase from Oat Seeds", Biotech. Letters, 11:7, 487–492 (1989). This paper describes the specificity of seed lipases for monounsaturated fatty acids.

Lazar, G. and Eirich, L. D., "Hydrolysis of tallow, olive oil and coconut oil by extracellular, intracellular and membrane-bound microbial lipases-lipase-catalyzed lipid hydrolysis (conference abstract), Biol. Chem. Hoppe Seyler (1989), 370, 9, 985 (Henkel).

"The substrate specificity of extracellular, intracellular and membrane-bound lipase (EC-3.1.1.3)-containing fractions of . . . *Geotrichum candidum* was determined using tallow, olive oil and coconut oil as substrates. After limited enzymatic hydrolysis of the triglycerides, the proportion of fatty acids were determined and compared to the total chemical hydrolysis . . . [A]11 lipases from *G. candidum* showed a very strong specificity for oleic and linoleic acids. Thus, different lipase fractions from a particular microorganism can have very different substrate specificities and, to a certain extent, substrate specificities are dependent upon the triglyceride hydrolyzed."

Jacobsen et al., Enzyme Microb. Technol. (1989) 11,90–95. This paper characterizes several enzymes from a general strain *G. candidum*. Oil induction of enzyme production by *G. candidum* was utilized to prepare the enzyme, distinguishing from Henkel's innovative enzyme production. Finally, the article is solely related to "extracellular" lipase and fails to examine selectivity between palmitic and oleic acid.

Baillargeon et al., "Evaluation of strains of *Geotrichum candidum* for lipase activity and fatty acid specificity", App. Microbiol. Biotech., 30, 92–96 (1989). This article examines three *Geotrichum candidum* strains, namely ATCC34614, NRRL Y-552 and NRRL Y-553. Using two crudely prepared commercial lipases as controls, the researchers did not observe any discrimination of the lipases from the strain utilized by Henkel, NRRL Y-522 or ATCC 34614. The researchers did observe preferential specificity for hydrolysis in NRRL Y-553.

The researcher utilized enzymatic reaction rates for pure oleic and palmitic acids, then comparing the ratios of the specificity constants. The rates of Y-553 were significantly higher than those prepared from Y-552, which only preferred oleic acid over palmitic acid at a ratio of 1.5 or not at all. This reference teaches away from the highly positive results of the mutant obtained from Y-552 by researchers at Henkel. Baillargeon states that the "specificity of the *G. candidum* lipases apparently varies greatly with strain." Baillargeon also states that relative rate ratios in the range of 10–15:1 would be "industrially useful for the separation of unsaturated fatty acids."

Hills, "Enzymatic Fractionation of Evening Primrose Oil by Rape Lipase: Enrichment of Gamma-Linolenic Acid", Biotechnology Letters, 2:9, 629–632 (1989). Rape lipase catalyses the production of esterification of oleic acid with butanol 35 times faster than GLA (Gamma-Linolenic Acid).

Jacobsen et al., Biotechnology Letters 12, 121–126 (1990) produced a hydrolytic rate for the methyl esters of oleic acid 10 times better than the rates for palmitic methyl ester. However, no rates for natural or synthetic triglycerides were reported.

U.S. Pat. Nos. 4,719,178 and 4,861,716 describe the use of *G. candidum* as for the hydrolysis of esters of a particular type of long chain fatty acid; U.S. Pat. No. 4,683,987 describes the use of lipase from *G. candidum* in the esterification of 2-halopropionic acid. U.S. Pat. No. 4,275,081 teaches the use of *G. candidum* in the randomization of fatty acid radicals in the glyceride position and U.S. Pat. No.

4,275,011 utilized *G. candidum* in the production of glyceride.

SUMMARY OF THE INVENTION

The present invention relates to a novel strain of *Geotrichum candidum* ATCC No. 74170 as well as novel enzyme UNLipase, an extracellular oleic acid-selective lipase produced by this organism. This invention also includes within its scope a novel process for the production of the mutant strain.

The process for the production for this novel strain comprises a.) culturing *Geotrichum candidum* NRRL Y552 in a nutrient medium, e.g. nutrient agar;

b.) exposing the cultured strain to ultraviolet light for a sufficient period of time to induce mutation;

c.) incubating the resulting mutants with agitation in a nutrient broth;

d.) freezing the suspension;

e.) thawing the suspension and f.) repeating steps a.) through e.), yielding the desired organism.

The nutrient broth comprises a mixture of about 1% to about 10% by weight of partially hydrolyzed proteins suitably from animal or vegetable origin (peptones), e.g. trypticase peptone, bactopeptone, soy peptone, casamino acids, NZ-amine® or casein in water. A 5% trypticase peptone in water is the nutrient broth typically employed.

The UNLipase according to the present invention is particularly useful in obtaining high purity oleic acid from fats and oils with the advantages of a) requiring low temperatures (23°–45° C.) and b) requiring neutral pH (6.0–8.0) yielding a product stream of oleic and linoleic acids with saturated mono-, di- and triglycerides. Furthermore, the catalyst can be immobilized rendering it suitable for cycling in either a batch or continuous mode of operation. The oleic acid selective lipase can be used for the selective esterification of oleic acid and other unsaturated fatty acids from mixtures of saturated and unsaturated fatty acids. UNLipase can also be used for the selective transesterfication of esters of oleic acid from mixtures of saturated and unsaturated esters.

DETAILED DESCRIPTION OF THE INVENTION

The present invention relates to a strain of *Geotrichum candidum* identified by ATCC deposit no. 74170 and the corresponding mutants and variants of this-strain as well as a novel lipase produced by the strain characterized by an increased selectivity for unsaturated fatty acid hydrolysis from triglycerides and other esters. The strain identified as *Geotrichum candidum* ATCC 74170 was deposited with the American Type Culture Collection, 12301 Parklawn Drive, Rockville MD 20852–1776, on Jul. 8, 1992. Included within the scope of this invention is a mutagenesis and selection process for the production of this strain. This invention also includes the process of selective hydrolysis of oleic and other unsaturated fatty acids from fats and oils utilizing this lipase of the invention.

The lipase product according to the present invention is identified as UNLipase.

The process for the production of the *G. candidum* mutant is as follows.

Source of *G. candidum* strain: *G. candidum* strains were obtained from the USDA culture collection in Peoria, Ill. In particular, the strain NRRL Y-552 (ATCC#74169) was chosen.

Culture media: Typically, the mutant strain of *Geotrichum candidum* NRRL Y-552 is prepared by culturing the strain in culture plates for 3 or 4 days in nutrient agar, rinsing off the culture plates with sterile water to obtain single-cell arthrospores, exposing the culture plates to ultraviolet light for a predetermined period of time to produce mutants, placing the mutants in a broth composed of 5% bactopeptone, shaking at eight degrees Celsius for twenty-four hours to create a suspension, freezing the suspension at–5 degrees Celsius, thawing the suspension, culturing mutants from the suspension, and repeating the process.

The novel mutant which is known by Henkel's internal number 9-2-3-9 as stated above is identified by the ATCC deposit no. 74170.

The desired UNLipase is hanFested from the cultured cells as follows

1. Enzyme Preparation

The Enzyme was harvested using centrifugation at 5000 rpms, for example, in a Beckman GSA rotor for 10 minutes. This cell-free preparation was used to determine hydrolysis, esterification and transesterification properties.

2. Substrate Preparation

Substrates were prepared in isooctane (2,2,4-trimethylpentane) at about 0.8 grams per 20 ml solvent. Assay procedures for determining lipase activity were those described by Kwon, D. Y. and Rhee, J. S., J. Amer. Oil Chem Soc. 63:89–92(1986). One modification was to perform some assays for one hour under nonagitated conditions to avoid difficulties in reproducing agitation rates.

The UNLipase has a molecular weight in the range of about 35,000 to 70,000 Daltons has a pH range of 5.0 to 9.5 with an optimal pH range of 7.5 to 8.5 and a temperature range of 0° to 40° C. with a $T_{max}$=32° C. It is inhibited by calcium ions at 25 mM concentration but activated by magnesium ions at concentration of 25 mM.

Selectivity of UNLipase

1. Hydrolysis of pure triglycerides with UNLipase

Pure triglycerides of caprylic (C8), caproic (C10), lauric (C12), myristic (C14), palmitic (C16), stearic (C18), arachidonic (C20), palmitoleic (C16:1), oleic (C18:1) and linoleic (C18:2) were prepared as described under "substrate preparation" and reacted with UNLipase in the presence of water for 1 hour at 37 degrees C. Hydrolysis was greatest for triolein, with the ratio of hydrolysis for triolein:tripalmitolein:trilinolein of 100:65:82. Of the saturated fatty acid triglycerides, only tripalmitin showed any reactivity with UNLipase. The ratio of hydrolysis of triolein to tripalmitin was approximately 33:1.

2. Hydrolysis of Common Acyl Triglycerides with UNLipase

Twenty grams of hard-bodied tallow, lard, palm kernel oil or peanut oil were treated with 5% (v/v) of cell free fermentation broth of mutant 9-2 which contained UNLipase. The reaction was run at 30 degrees C. for 22 hours, with mechanical agitation at about 200 rpm. Hard-bodied tallow was hydrolyzed, resulting in free fatty acids that were composed of 87% oleic acid and 13% other unsaturated fatty acids. Lard was hydrolyzed by UNLipase yielding free fatty acids which were 99% unsaturated. Palm kernel oil, which contains approximately 17% by weight unsaturated fatty acids in the triglycerides, was hydrolyzed by UNLipase to yield free fatty acids which were 97% unsaturated. Peanut oil, which is 80% oleic and linoleic acids by weight, was hydrolyzed by UNLipase to yield free fatty acids which were 100% unsaturated.

3. Hydrolysis of Simple Esters with UNLipase

Simple esters were subjected to UNLipase to determine the scope and extent of UNLipase selectivity. The esters evaluated were methyl esters of propionic, caprylic, nonanoic, caproic, palmitic and oleic acids. Esters were prepared at about 50 mM in isooctane and subjected to UNLipase at 37 degrees C. for 4 hours. Only the methyl ester of oleic acid demonstrated any appreciable hydrolysis as catalyzed by UNLipase. The methyl esters of propionic, caprylic, caproic and nonanoic acids were not hydrolyzed by UNLipase. Approximately 2% of the methyl palmitate reacted, whereas 67% of the methyl oleate was hydrolyzed.

4. Esterification and Transesterification of UNLipase

Concentrated aqueous preparations of lipase were used to test the ester synthesis properties of UNLipase. These preparations contained 50–200 mg of fatty acid, 0.5 ml concentrated broth, 0.5 ml water (buffer) and 100–300 ul of alcohol. Reactions were run at either 27, 30 or 37 degrees Celsius for 16 to 24 hours. The reaction was stopped by adding 2.0 ml ether.

Fatty acid and ester were extracted into ether and evaluated by thin layer chromatography. The esterification of oleic acid with various alcohols is present in Table 1. The results indicate that oleic esters were synthesized with 1° and 2° alcohols, even cyclic alcohols, but the one tertiary alcohol tested did not react with oleic acid in the presence of lipase.

TABLE 1

Alcohol Selectivity of Oleic Acid Esterification

| Alcohol | Ester Formed |
|---|---|
| Methanol | + + + + |
| Ethanol | + + + + |
| n-butanol | + + |
| 2-octanol | + + + + |
| 3-pentanol | + + + + |
| Glycerine | + + + |
| Cyclohexanol | + + |
| t-butanol | — |

The fatty acid selectivity of the lipase in esterification reactions was also evaluated in the manner described above, with results analyzed by thin layer chromatography, GC, HPLC and IR. The results are presented below in Table 2.

TABLE 2

Fatty Acid Selectivity of Lipase Esterification

| Fatty Acid | Geometry | Ester Formation |
|---|---|---|
| Oleic | cis, 9, 10 | + + + + |
| Elaidic | trans, 9, 10 | — |
| Petroselenic | cis, 6, 7 | — |
| Vaccenic | cis, 11, 12 | — |
| Undecenoic acid | 10, 11 | — |
| Palmitoleic | cis, 9, 10 | + + + + |
| Linoleic | cis, 9, 10; 12, 13 | + + + + |
| Linolenic | cis, 9, 10; 12, 13; 15, 16 | + + + + |
| Gamma Linolenic | cis, 6, 7; 9, 10; 12, 13 | — |
| Oleic + Undecenoic acid | | ++ |

The conclusions which can be drawn from these data are the lipase has a highly defined selectivity not only for the position of the double bond but the geometry. The selectivity appears to be strictly a cis 9, 10 double bond in monounsaturated fatty acids. For polyunsaturates, the cis 9, 10 bond is also required, however, the lack of reactivity of gamma linolenic indicates that in addition to the cis 9, 10 double bond, a double bond between the carbonyl carbon and the 9,10 double bond is not tolerated. A double bond removed by only one carbon, 10-undecenoic acid, disrupts the chemistry of the active site.

In fact, 10-undecenoic acid acts as an inhibitor of the esterification of oleic acid, this suggests that the interaction between the enzyme and the double bond is occurring, causing the inhibition.

Collectively, the reactivities outlined above suggest a model of the active site. Reactivity (esterification) requires an interaction between a double bond and some site on the enzyme. One possible explanation is that this interaction anchors the fatty acid substrate in place and positions the reactive carbonyl carbon at the catalytic site of the enzyme.

The esterification of fatty acid mixtures was evaluated using typical fatty acid mixtures derived from pressure-split beef tallow, henceforth referred to as PFA. Samples of PFA were spiked with pentadecanoic acid as an internal standard. The resulting products were analyses by either HPLC (reverse phase C-18 column) or GC (FFAP capillary column). Only esters of oleic, palmitoleic and linoleic acids were detected. Linolenic acid concentration in the PFA was deemed too low to be able to determine ester formation. Stearic, palmitic, myristic and pentadecanoic acid (internal standard) were not esterified. Thus, complex mixtures of fatty acids can be treated with the selective lipase to yield only esters of fatty acids containing the cis 9, 10 double bond.

5. Purification of UNLipase

UNLipase was purified from fermentation broth after removal of the cell mass by centrifugation by applying the following series of steps:

A. Biocryl BPA-1000 cation exchange chromatography to clarify the cell-free broth of nonproteinaceous material;

B. Concentration of the UNLipase by ethanol precipitation followed by centrifugation;

C. Resuspension of the ethanol precipitation, followed by hydrophobic interaction chromatography on octyl-sepharose;

D. Chromatography on Q-Sepharose with final concentration of the lipase by ultrafiltration using Centricon 30 ultrafiltration units.

A single protein band was confirmed by electrophoresis. Analytical isoelectric focusing indicated two major and two minor isozymes in the ph range of 4.0–4.6. Chromatofocusing isolated the major isozyme (pI=4.5) which demonstrated the highest degree of selectivity for oleic acid. The enzyme (UNLipase) had a molecular weight of approximately 65,000 kDa with sites of glycosylation which were sensitive to endoglycosidase H.

In order to illustrate the practice of this invention, the following examples are included.

EXAMPLE 1

Strain NRRL Y-552 was grown on nutrient agar for 3 to 4 days. Single-cell arthrospores were then rinsed from the surface of the plates with sterile distilled water. The cells were then used to determine the time of exposure to UV light that was required for a 90% kill (indicating highly successful mutagenesis). This was done in the biosafety hood (Nuaire) which is equipped with a UV light. Five mls of the arthrospore suspension were placed in sterile petri dishes then exposed to the UV light for various periods of time. It was determined that 90 seconds of exposure resulted in better than 90% kill rates. The mutants thus produced were added to 50 mls of bacto-peptone broth (5%) and placed on a shaker at 8° C. for 24 hours. (This was given as a recovery time for the survivors.) The UV irradiated suspensions were then placed in sterile 50 ml test tubes and frozen at −5° C. Of the few UV irradiated survivors more than 99.9% were killed by exposure to the freezing treatment. (The hypothesis for survival was that the membranes highest in unsaturated fatty acids would provide an advantage to survival of the freezing conditions.) These few survivors were then screened for lipase production and fatty acid specificity in the standard lipase assay using triolein or tripalmitin as the substrate (assay described above). One mutant, 9-2, resulted which had better than a 25:1 selectivity for oleic acid versus palmitic acid (in this assay) when pure triglycerides of each were tested. This enzyme was designated "UNLipase" for its selection of unsaturated fatty acids.

Although the initial work with 9-2 resulted in growing the organism in a modified standard broth (Tsujisaka et al. 1973), work was undertaken to improve the production of the UNLipase enzyme. It was determined early in our work that having fat or oil in the medium induced other lipases produced by Geotrichum strains. Thus fat or oil was eliminated from the medium. Then improvements for Bacto-Peptone were sought. A series of peptones or other organic nitrogen sources were tested including soy peptone, trypticase® (BBL) peptone, casamino acids, NZ amine® (Sheffield Products) and casein. It was determined that trypticase® peptone at 5% resulted in the highest levels of UNLipase production.

The next important discovery was that the addition of a sugar or sugar alcohol either had no effect on UNLipase production (e.g. mannitol and maltose) or actually inhibited UNLipase production (e.g. fructose, glucose, and sucrose). Next, the salt constituents were examined in the standard medium. Additions of both $MgSO_4$ at 0.05% (w/v) and $KH_2PO_4$ at 0.1% (w/v) were shown to benefit the production of the enzyme. The inclusion of these two salts in the medium gave a doubling of measured hydrolytic activity when assayed using the standard assay. Increasing the concentration of $MgSO_4$ to 0.5% gave no further enhancement. It was found that calcium additions (0.1 to 0.5%) to the medium did not enhance the lipase production. Thus the UNLipase enzyme can be produced routinely in a medium containing 5% trypticase peptone, 0.1% $MgSO_4$, 0.5% KH2PO4 with no pH adjustment. Fifty mls of this medium are placed in 500 ml baffled flasks (Bellco) then shaken at 250 rpms at 25°–30° C.

The UNLipase enzyme was produced and optimized in mutant 9-2. The next goal was to find a mutant with enhanced productivity. Thus the mutagenesis of mutant 9-2 was undertaken as described above but the selection protocol was altered. In this case, after the 8° C. recovery period the mutant suspensions were placed in 50 ml sterile test tubes and frozen at −55° C. The period of freezing was then interrupted by thawing periods (about 4 hours) and followed by freezing at −55° C. Mutants were screened for lipase activity and selectivity. One mutant, 9-2-3-9, survived a cycle of 3 weeks of freezing which had been interrupted by 3 thaw cycles. The mutant 9-2-3-9 was distinctly different from its parent (9-2) in its colony morphology when grown on nutrient agar. The colony type was much more aerial than 9-2. The most distinctive feature was that this mutant, although it produced less cell mass when grown in culture than 9-2, actually expressed much more enzyme activity.

EXAMPLE 2

The mutant 9-2 was grown in the medium described above. Fifty mls were added to 500 ml baffled flasks (Bellco) and placed on a shaker maintained at 30° C. and shaken at 250 rpms. Production reaches a peak at about 30 hours, then declines slightly and remains low. The enzyme was harvested at 30 hours for a series of hydrolytic tests. The collection of the enzyme involves centrifugation of the broth at 5000 rpms in the Beckman GSA rotor for 10 minutes. The cell free broth was then decanted from the cell pellet. In some cases, high activity suspension were produced by a 70% ammonium sulfate precipitation of the broth.

EXAMPLE 3

To demonstrate the practical aspects of UNLipase selective fat splitting, ten pounds of edible lard was placed in a 15 liter reaction vessel with temperature control at 30 degrees C and agitation rates of between 300–500 rpm. Cell-free fermentation broth from culture of mutant 9-2 or twice-concentrated cell-free broth was added to initiate the hydrolysis. The broth provided the necessary water of reaction. Hydrolysis progress was monitored periodically by determining the acid value (AOCS Method Te 1a-64) of an aliquot of the reaction mixture. The composition of free fatty acids at the end of the reaction was 99% unsaturated fatty acids. The ratio of oleicpalmitoleiclinoleic was 78:3:18.

What is claimed is:

1. A biologically pure culture of a strain of *Geotrichum candidum* having all the identifying characteristics of the strain ATCC 74170.

2. The biologically pure culture of claim 1 wherein said strain is *Geotrichum candidum* ATCC 74170.

* * * * *

UNITED STATES PATENT AND TRADEMARK OFFICE
CERTIFICATE OF CORRECTION

PATENT NO. : 5,470,741
DATED : Nov. 28, 1995
INVENTOR(S) : Dean A. Oester, Allen L. Hall, Stephen J. Vesper It is certified that error appears in the above-indentified patent and that said Letters Patent is hereby corrected as shown below:

In col. 6, line 19, delete [hanFested] and insert --harvested--.

In col. 10, line 46, delete [oleicpalmitoleiclinoleic] and insert --oleic:palmitoleic:linoleic--.

Signed and Sealed this

Fifth Day of November, 1996

Attest:

BRUCE LEHMAN

*Attesting Officer*  *Commissioner of Patents and Trademarks*